(12) United States Patent
Dejongh et al.

(10) Patent No.: US 10,918,350 B2
(45) Date of Patent: Feb. 16, 2021

(54) PROCESSING PIPELINE FOR PROMPT PARTICLE IMAGE RECONSTRUCTION

(71) Applicants: BOARD OF TRUSTEES OF NORTHERN ILLINOIS UNIVERSITY, Dekalb, IL (US); PROTONVDA Inc., Naperville, IL (US)

(72) Inventors: Don F. Dejongh, Batavia, IL (US); Ethan A. Dejongh, Batavia, IL (US); Kirk Duffin, Batavia, IL (US); Nicholas Karonis, Batavia, IL (US); Caesar Ordoñez, Batavia, IL (US); John Winans, Batavia, IL (US)

(73) Assignees: BOARD OF TRUSTEES OF NORTHERN ILLINOIS UNIVERSITY, Dekalb, IL (US); PROTONVDA LLC, Naperville, IL (US)

( * ) Notice: Subject to any disclaimer, the term of this patent is extended or adjusted under 35 U.S.C. 154(b) by 189 days.

(21) Appl. No.: 16/233,533

(22) Filed: Dec. 27, 2018

(65) Prior Publication Data

US 2019/0200946 A1 Jul. 4, 2019

Related U.S. Application Data

(60) Provisional application No. 62/611,475, filed on Dec. 28, 2017.

(51) Int. Cl.
*A61B 6/00* (2006.01)
*A61B 6/03* (2006.01)

(52) U.S. Cl.
CPC ............ *A61B 6/5205* (2013.01); *A61B 6/032* (2013.01); *A61B 6/4071* (2013.01);
(Continued)

(58) Field of Classification Search
None
See application file for complete search history.

(56) References Cited

U.S. PATENT DOCUMENTS 4,829,185 A 5/1989 Kerff
5,264,702 A 11/1993 Mihalczo
(Continued)

FOREIGN PATENT DOCUMENTS

EP 2746816 6/2014
WO WO 2011/100628 8/2011
(Continued)

OTHER PUBLICATIONS

Coutrakon et al., "Design and construction of the 1st proton CT scanner," AIP Conference Proceedings, (Jan. 1, 2013) pp. 327-331, New York, US.
(Continued)

*Primary Examiner* — Fayyaz Alam
(74) *Attorney, Agent, or Firm* — Barnes & Thornburg LLP; Alice O. Martin

(57) ABSTRACT

A computer-implemented system and method for generating a medical image is provided. In some embodiments, the medical image is generated by determining a location and an alignment for a first tracking detector with respect to a particle beam system. The direction of a beam generated from the particle beam system is determined. A first position of a first particle from a detected particle hit on the first tracking detector is also determined. A determination is made as to a first residual range of the first particle from a detected particle hit on a residual range detector. The system reconstructs a path for the first particle based on the location, the alignment, the first position, and the first residual range
(Continued)

of the first particle. The resulting medical image that is generated by the system is based on the reconstructed path for the first particle.

46 Claims, 7 Drawing Sheets

(52) U.S. Cl.
CPC ............ *A61B 6/4258* (2013.01); *A61B 6/547* (2013.01); *A61B 6/587* (2013.01); *A61B 6/588* (2013.01)

(56) References Cited

U.S. PATENT DOCUMENTS

| | | | |
|---|---|---|---|
| RE36,201 E | 4/1999 | Miller | |
| 6,078,052 A | 6/2000 | DiFilippo | |
| 9,207,193 B2* | 12/2015 | Censor | A61N 5/10 |
| 9,333,376 B2* | 5/2016 | Boisseau | A61N 5/1075 |
| 9,880,301 B2 | 1/2018 | Schulte | |
| 2003/0147618 A1 | 8/2003 | Guy | |
| 2006/0108509 A1 | 5/2006 | Frangioni | |
| 2009/0266992 A1 | 10/2009 | Beekman | |
| 2013/0015352 A1 | 1/2013 | Karonis | |
| 2015/0170359 A1* | 6/2015 | Star-Lack | G06T 7/0012 382/131 |
| 2015/0213630 A1* | 7/2015 | Szirmay-Kalos | G06T 1/20 382/131 |
| 2015/0246244 A1 | 9/2015 | Sossong | |
| 2015/0251021 A1* | 9/2015 | Boisseau | A61N 5/1075 250/252.1 |
| 2015/0369744 A1 | 12/2015 | Yang | |
| 2016/0338654 A1* | 11/2016 | Dejongh | A61B 6/4216 |
| 2017/0160211 A1* | 6/2017 | Schulte | A61B 6/5205 |
| 2017/0221230 A1* | 8/2017 | Allinson | G06T 11/00 |

FOREIGN PATENT DOCUMENTS

| | | |
|---|---|---|
| WO | WO 2011/162851 | 12/2011 |
| WO | WO 2013/186798 | 12/2013 |
| WO | WO 2015/195570 | 12/2015 |

OTHER PUBLICATIONS

Hurley et al., "Water-equivalent path length calibration of a prototype proton CT scanner," Medical Physics, AIP, 39(5): 2438-2446 (May 1, 2012).

Plautz et al., "200 MeV Proton Radiography Studies with a Hand Phantom Using a Prototype Proton CT Scanner," IEEE Transactions on Medical Imaging, IEEE Service Center, 33(4): 875-888 (Apr. 1, 2014).

Pemler et al., "A detector system for proton radiography on the gantry of the Paul-Scherrer-Institute," Nuclear Instruments & Methods in Physics Research, Section A: Accelerators, Spectrometers, Detectors, and Associated Equipment, vol. 432(2-3): 483-495 (Aug. 11, 1999).

Sadrozinski, et al., "Detector development for Proton Computed Tomography (pCT)," Nuclear Science Symposium and Medical Imaging Conference (NSS/MIC), 2011 IEEE, pp. 4457-4461 (Oct. 23, 2011).

Search and Written Opinion issued in Int'l App. No. PCT/US2018/067628 (2019).

Uzunyan et al., "A New Proton CT Scanner," 23rd Conference on Application of Accelerators in Research and Industry, CAARI 2014, (Aug. 29, 2014) 6 pages, San Antonio, Texas. Retrieved from: http:/larxiv.org/pdf/1409.0049v2.pdf (retrieved on Jul. 18, 2016).

* cited by examiner

PROCESSING PIPELINE FOR PROMPT PARTICLE IMAGE RECONSTRUCTION

RELATED APPLICATIONS

This application claims the benefit of U.S. Provisional Patent Application Ser. No. 62/611,475 filed Dec. 28, 2017 for a "Processing Pipeline for Prompt Particle Image Reconstruction," which is hereby incorporated by reference in its entirety.

STATEMENT REGARDING FEDERALLY SPONSORED RESEARCH OR DEVELOPMENT

This invention was made with government support from the National Cancer Institute of the National Institutes of Health under Award Number R43CA203499. The government has certain rights in the invention.

TECHNICAL FIELD

This disclosure relates to medical imaging systems; in particular, this disclosure relates to technology for generating medical images from proton/particle radiography.

BACKGROUND

Radiation therapy is needed for more than 50% of the 1.6 million Americans who are annually diagnosed with cancer. A conservative estimate from the Mayo Clinic is that 137,000 new cancer patients each year in the United States could benefit from proton therapy, well above current capacity. Proton radiation therapy can potentially spare large amounts of normal tissue from low to intermediate radiation dose and avoid organs at risk. This reduces late effects and improves quality of life, and is especially important for patients with high cure rates and long survival times. A recent policy statement issued by the American Society of Therapeutic Radiation Oncology (ASTRO) cites scientific evidence confirming that proton beam therapy is particularly useful in a number of pediatric patients, particularly those with brain tumors, as well as for certain adult cancers requiring high doses in close proximity to critical structures. Additional research on more common cancer disease sites, such as breast, prostate and lung, is ongoing, with NCI-supported clinical trials accruing patients in all three disease sites from proton therapy facilities in the U.S. Currently, 73 ion therapy facilities (62 proton, 11 carbon) are in operation worldwide (25 proton in the U.S.) with 42 (40 proton, 1 carbon, 1 proton&carbon) under construction (10 proton in U.S.) and 22 (21 proton, 1 carbon) in the planning stages (4 proton in U.S.).

The Bragg peak phenomena (the sharp dose peak that occurs at the end of a particle's range) enables particles such as protons and other ions (e.g., deuterons, helium, or carbon) to precisely target tumors for radiation therapy, while healthy tissues receive a minimal dose when compared with x-ray therapy systems. Proton radiation therapy however requires precise patient alignment, and also adjustment of initial proton energy so that the maximum dose corresponding to the Bragg peak is deposited in intended tissues. In order to adjust the range of a proton beam, so that the maximum dose corresponding to the Bragg peak is deposited in intended tissues, treatment planning may require a three-dimensional map of a particular patient in terms of relative stopping power (the energy loss of the proton beam in a material relative to that of water).

SUMMARY

According to one aspect, this disclosure provides a computer-implemented method for generating a medical image. The method includes the step of determining a location and an alignment for a first tracking detector with respect to a particle beam system. A first position of a first particle generated from the beam system is determined, from a detected particle hit on the first tracking detector. The first direction of the first particle at the first tracking detector is determined. The method includes the step of determining a first residual range of the first particle from a detected particle hit on a residual range detector. A path for the first particle is reconstructed based on the location, the alignment, the first position, and the first direction. The medical image is generated based on the reconstructed path for the first particle and the first residual range of the first particle.

According to another aspect, this disclosure provides one or more non-transitory computer-readable storage medium comprising a plurality of instructions that in response to being executed cause a computing device to: determine a location and an alignment for a first tracking detector with respect to a particle beam system; determine a first position of a first particle generated from the beam system, from a detected particle hit on the first tracking detector; determine a first direction of the first particle at the first tracking detector; determine a first residual range of the first particle from a detected particle hit on a residual range detector; reconstruct a path for the first particle based on the location, the alignment, the first position, and the first direction; and generate the medical image based on the reconstructed path for the first particle and the first residual range of the first particle.

According to a further aspect, this disclosure provides a computing system for generating a medical image. The computing system includes one or more processors and a memory having a plurality of instructions stored thereon that, when executed by the one or more processors, causes the computing system to: determine a location and an alignment for a first tracking detector with respect to a particle beam system; determine a first position of a first particle generated from the beam system, from a detected particle hit on the first tracking detector; determine a first direction of the first particle at the first tracking detector; determine a first residual range of the first particle from a detected particle hit on a residual range detector; reconstruct a path for the first particle based on the location, the alignment, the first position, and the first direction; and generate the medical image based on the reconstructed path for the first particle and the first residual range of the first particle.

BRIEF DESCRIPTION OF THE DRAWINGS

The present disclosure will be described hereafter with reference to the attached drawings which are given as non-limiting examples only, in which.

Figure 1:
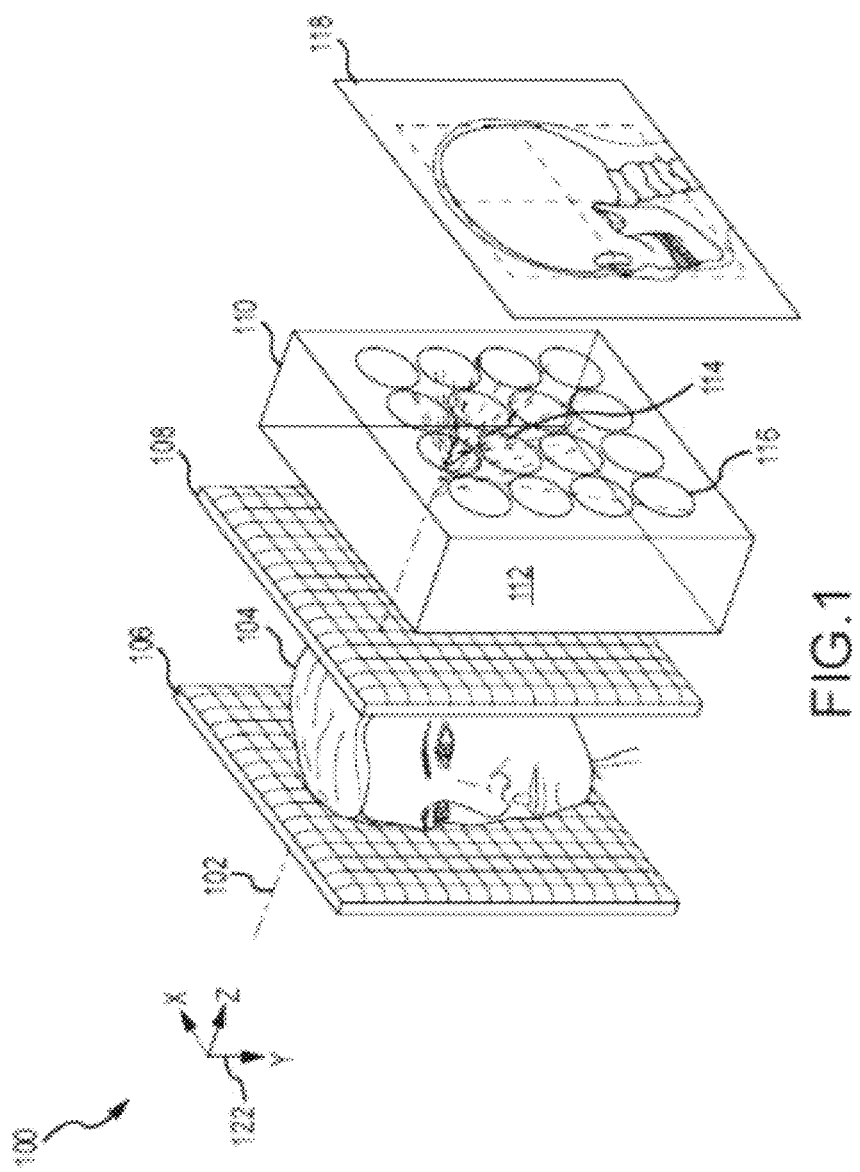
FIG. 1 shows a proton radiography system according to the disclosure.

Corresponding reference characters indicate corresponding parts throughout the several views. The components in the figures are not necessarily to scale, emphasis instead being placed upon illustrating the principals of the invention. The exemplification set out herein illustrates embodiments of the invention, and such exemplification is not to be construed as limiting the scope of the invention in any manner.

DETAILED DESCRIPTION

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

Proton (and other particle) radiation therapy requires a three-dimensional map of the patient in terms of relative stopping power (RSP) (the energy loss of the beam in a material relative to that of water) for treatment planning. This information is used to adjust the range of the ion beam. In some cases, these maps are obtained from x-ray CT scans. Such maps introduce uncertainties relating to conversion of x-ray absorption (Hounsfield) units to RSP and inhomogeneities in the patient add additional uncertainties. Furthermore, metallic implants or other high-density materials can cause shadowing artifacts and streaking.

Exemplary techniques described below, reduce alignment uncertainties, reduce range uncertainties, and enable more complex treatments using more ion directions and delivering a higher dose to the tumor per treatment. In addition to the benefits of a direct measurement of proton stopping power, proton imaging deposits much less dose to the patient relative to x-ray images of comparable resolution. The use of a proton beam for both imaging and treatment streamlines patient setup and quality assurance procedures, reduces alignment uncertainties, and reduces range uncertainties.

Proton trajectories deviate from straight lines due to multiple Coulomb scattering, and forming the images with optimal spatial resolution is therefore more complicated than for x-ray radiographs.

Some embodiments of the technology described below avoid the need for a large amount of analysis and to apply calibrations and convert raw data to proton paths and residual ranges. Some embodiments allow for images to be produced promptly for verification just prior to a treatment immediately after data acquisition, which was not previously possible.

FIG. 1 depicts system 100, which is an embodiment of a proton radiography system according to the present technology. In some examples, a pencil beam 102 (alternatively, a broad beam could also be used with variations of the present technology) of protons (although other particles, such as heavy ions, could also be used) is generated or extracted from a source (see FIG. 2) and scanned across a field by a scanning element (see FIG. 2). For example, pencil beam 102 is scanned across a region of interest of object 104, which is a human head in FIG. 1. The position of pencil beam 102 as it enters object 104 can be determined based on data from tracking detector 106 that generates photons at locations where protons traverse tracking detector 106, as described in more detail below. Similarly, the position of pencil beam 102 as it exits object 104 can be determined using data from tracking detector 108. Note that tracking detectors 106 and 108 are spaced apart to allow object 104 to be positioned between them. In some embodiments, only one tracking detector is needed or two or more tracking detectors are used on one or both sides of object 104. In the case of only a single tracking detector, a direction of the pencil beam can be used to determine the direction for each ion. Potential architectures for tracking detectors 106 and 108 are described in more detail below.

Residual range detector 110 is positioned adjacent tracking detector 108. Residual range detector 110 includes scintillator material 112 (represented in FIG. 1 by a box). In one example, the scintillator material may be one sold by Eljen Technology of Sweetwater, Tex., USA. As a proton of pencil beam 102 enters scintillator material 112 through the surface facing tracking detector 108, the proton generates photons 114 (represented by dotted lines in FIG. 1) as the protons loses energy from interacting with scintillator material 112. These photons can then be collected by photon detectors (FIGS. 2 and 5) coupled to scintillator material 110 on the surface of scintillator material 112 that is opposite the surface facing tracking detector 108. The coupling of the photon detectors is depicted in FIG. 1 by circles 116. The signal generated by the photon detectors is proportional to a residual energy of a proton as it entered scintillator material 112. This information combined with the initial energy of the proton and the location of the proton as it entered and exited object 104, along with similar information for many additional protons, can be used to generate image 118 of object 104. By using multiple proton energies and/or protons at different angles (e.g., 100 different angles) in a proton tomography system using the present technology, 3D images can also be produced.

Figure 2:
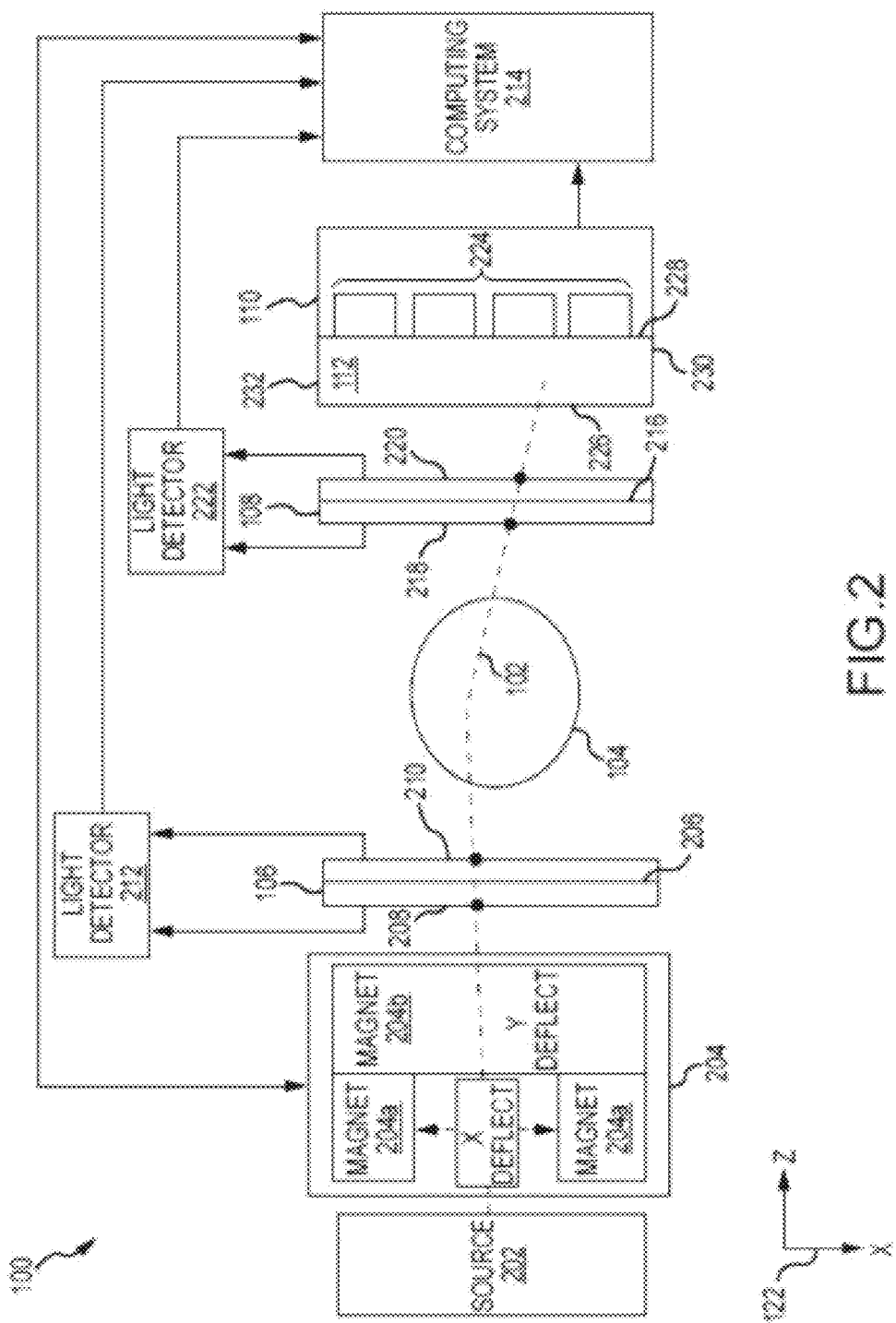
FIG. 2 shows the system of FIG. 1 in more detail and in block diagram form.
Figure 3:
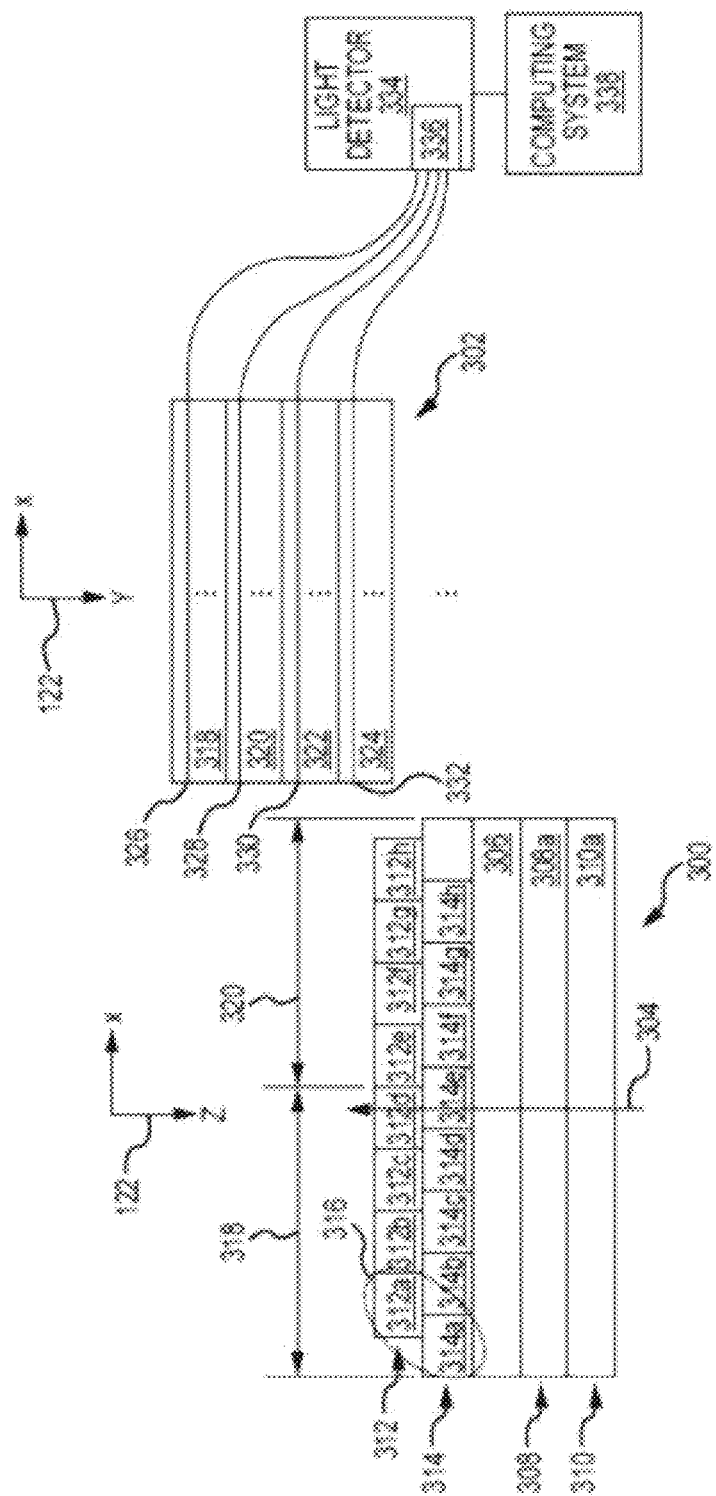
FIG. 3 shows multiple views of a tracking detector of the system of FIG. 1.

Note that reference axes 122 show that pencil beam 102 is traveling along the z-axis and tracking detectors 106 and 108 are perpendicular to the z-axis. FIGS. 2 and 3 described below will be described with respect to the same reference axes.

FIG. 2 depicts system 100 of FIG. 1 with additional detail and from a different perspective, as indicated by reference axes 122. With reference to FIG. 2, system 100 includes source 202 that generates or extracts pencil beam 102. Scanning element 204 is used to steer pencil beam 102 and includes scanning magnets 204a and 204b. Scanning magnets 204a scan the pencil beam 102 in x-directions as defined with respect to reference axes 122, and scanning magnets 204b (the second of which is hidden in the perspective of FIG. 2) scan pencil beam 102 in y-directions as defined with respect to respect to reference axes 122. In general, scanning element 106 is programmable such that pencil beam 102 is scan-able across the entirety of the field in any pattern, and, as determined by source 202, at any initial energy at any point in time. In this example, source 202 is capable of controlling or varying the initial energy of the protons of pencil beam 102. During a scan, the extent of the field is in general limited by the planar dimensions of first tracking detector 106, second tracking detector 108, or residual range detector 114 of system 100. Example field areas include 10×10 cm$^2$ to 38.4×38.4 cm$^2$.

By using a different initial energy at different transverse positions of the tracking detectors and the object being imaged, the residual range of the ions can be kept low and the depth of the residual range detector can be kept small. For example, the initial energies can be chosen to keep the residual range between 0 and 10 cm across the field to be imaged regardless of the thickness or density of the object along a particular path. The more range in initial energy that is possible, smaller residual range detectors may be possible.

In some examples of an architecture for tracking detector 106, as protons of pencil beam 102 traverse first tracking detector 106, the protons interact with fibers either side of substrate 206. Specifically, each side of substrate 206 includes, for example, two layers of fibers, i.e., fibers 208 on one side and fibers 210 on the opposite side of substrate 206. Fibers 208 and 210 may be scintillating fibers so that when a proton impinges a fiber, the scintillating properties of the fiber will cause one or more photons to be generated. These photons are captured by light detector 212, which generates an electrical signal based on the detected photons. The electrical signal is transmitted to computing system 214. By knowing the location and orientation of fibers 208 and 210 that produced photons, the location of the proton that traversed tracking detector 106 may be determined by computing system 214. Additionally, computing system 214 may also use data from scanning element 204 to determine or verify the location where a proton passed through tracking detector 106. Once the location is known the initial directional vector of pencil beam 102 can also be determined based on the focal point of source 202.

In some examples, fibers 208 are oriented perpendicular to fibers 210. If light detector 212 indicates that a proton passed through one fiber of fibers 208 and one fiber of fibers 210 and computing system 214 knows the location of these two fibers, computing system 214 can determine that the X-Y coordinate on tracking detector 106 where the proton traversed tracking detector 106 is at the intersection of the two fibers. Additionally, if fibers of fibers 208 or fibers of fibers 210 are connected together to reduce the number of detectors needed in light detector 212, then the estimated expected position of pencil beam 102 based on data from or instructions sent to scanning element 204 may be used in determining the X-Y coordinate where the proton traversed tracking detector 106, as described in more detail below with respect to FIG. 3.

As protons of pencil beam 102 traverse object 104, protons may be scattered, as is depicted in FIG. 2 as an exaggerated change in direction of pencil beam 102 in object 104. After the protons exit object 104, the exit location where protons traverse tracking detector 108 can be determined in a similar manner as described above with respect to tracking detector 106. Similar to tracking detector 106, tracking detector 108 includes fibers on substrate 216. Specifically, each side of substrate 216 includes, for example, two layers of fibers, i.e., fibers 218 on one side and fibers 220 on the other side of substrate 216. Fibers 218 and 220 may be scintillating fibers so that when a proton impinges a fiber, the scintillating properties of the fiber will cause one or more photons to be generated. These photons may be captured by light detector 222, which may generate an electrical signal based on the detected photons. The electrical signal is transmitted to computing system 214. By knowing the location and orientation of fibers 218 and 220 that produced photons, the location of the proton that traversed first tracking detector 108 may be determined by computing system 214. Additionally, computing system 214 may also use information from scanning element 204 to determine or verify the location on tracking detector 108 where a proton passed through tracking detector 108.

In some examples, fibers 218 are oriented perpendicular to fibers 220. If light detector 222 indicates that a proton passed through one fiber of fibers 218 and one fiber of fibers 220 and computing system 214 knows the location of these two fibers, computing system 214 can determine that the X-Y coordinate on tracking detector 108 where the proton traversed tracking detector 108 is at the intersection of the two fibers. Additionally, if fibers of fibers 218 or fibers of fibers 220 are connected together to reduce the number of detectors needed in light detector 222, then the estimated or expected position of pencil beam 102 based on data from or instruction sent to scanning element 204 may be used in determining the X-Y coordinate on tracking detector 108 where the proton traversed tracking detector 108, as described in more detail below with respect to FIG. 3.

While an exemplary architecture of a tracking detector has been described, other architectures are possible. For example, if fibers are rigid enough, the fibers could be bonded together to avoid using a substrate. As another example, with respect to tracking detector 106, fibers 208 and 210 could be placed on the same side of substrate 206 or fibers 208 and 210 could be placed on separate substrates that are placed next to each other.

As protons of pencil beam 102 enter residual range detector 110, they impinge scintillator material 112 and generate photons that are collected by photon detectors 224 (while four photon detectors are depicted in FIG. 2, system 100 includes sixteen photon detectors as indicated by the circles representing the photon detectors couplings to scintillator material 112 in FIG. 1). Photon detectors 224 are, for example, photomultiplier tubes or other similar devices. Photon detectors 224 generate electrical signals based on the number of photons collected and generate electrical signals that are provided to computing system 214, which may calculate values such as total energy. Based on the electrical signals, and potentially other information (such as the X-Y coordinate of where a proton exited object 104 and traversed tracking detector 108), computing system 214 may determine a residual energy for a proton of pencil beam 102 that entered scintillator material 112 after exiting object 104.

Protons enter scintillator material 112 via surface 226. Generated photons are collected by photon detectors 224 as the photon exit surface 228 of scintillator material 112. The dimensions of scintillator material 112 may be selected to ensure that protons stop in scintillator material 112 as opposed to passing through scintillator material 112. This ensures that protons of pencil beam 102 generate a large number of scintillation photons within a few nanoseconds. Surface 226, surface 230, surface 232, and/or the other two surfaces of scintillator material 112 not depicted in FIG. 2 are, in some examples, covered (e.g., deposited, coated, or arranged next) with an anti-reflective or photon absorbing material. For example, the walls of scintillator material 112 are painted black. The anti-reflective material ensures that mainly direct photons that have not scattered off the walls of scintillator material 112 are collected at photon detectors 224. The anti-reflective material may include different materials on different surfaces of scintillator material 112. In one example, the anti-reflective material may be Eljen Technology EJ510B black paint. The anti-reflective material may absorb 90% or more of the photons that contact the material. The anti-reflective material adds to the high speed operation of system 100.

The use of multiple photon detectors also provides the potential to obtain additional position data for the location that a proton exited object 104. For example, with reference to FIG. 1, if photon detectors are coupled to scintillator materials 112 as indicated by circles 116 (sixteen total), the photon detector nearest where the photon entered scintillator material 112 should produce the strongest signal. If the position of the photon detector that produces the strongest signal does not correlate with the position indicated by the signals generated from tracking detector 108 and light detector 222, then an event that should be rejected may exist, such as inelastic scatter.

FIG. 3 depicts two cross-sections of a tracking detector that may be used to implement tracking detectors 106 and 108 (FIGS. 1 and 2). Cross-section 300 depicts tracking detector along the plane parallel to the z-axis and x-axis, as depicted in reference axes 122. Cross-section 302 depicts the same tracking detector along the plane parallel to the y-axis and x-axis, as depicted in reference axes 122, which is also perpendicular to the plane of cross-section 300. Additionally, cross-section 302 is zoomed-out as compared to cross-section 300. In cross-section 300, the direction of protons is along the z-axis as depicted by path 304. In cross-section 302, the direction of protons is coming out of the figure.

As depicted in cross-section 300, the tracking detector includes a substrate 306 having two layers of fibers, 308 and 310, respectively, on one side and two layers of fibers, 312 and 314, respectively on the other side. Layers of fibers 308 and 310 are laid out perpendicular to layers of fibers 312 and 314. Only one fiber of layer of fibers 308 and one fiber of layer of fibers 310 are visible because the other fibers are blocked from view. Layer of fibers 312 includes fibers 312a-312h and layer of fibers 314 includes fibers 314a-314h. As depicted in FIG. 3, the layers of fibers on each side of the substrate may be offset from each other so that fibers of one layer (e.g., layer 312) are positioned between two fibers in the adjacent layer (e.g., layer 314). In other words, the fibers in one layer may be offset from the other layer by about one half the width of a single fiber. In this layout, protons that go through the interface between two fibers in one layer, should also go through the middle of the fiber in the next layer, which results in higher efficiency. Other architectures could have additional layers of fibers or only a single layer of fibers.

Fibers of adjacent layers can be bundled together so they connect to a single light detector channel. For example, with reference to FIG. 3, fibers 312a and 314a can be bundled together into fiber doublet 316 so fibers 312a and 314a connect to a single channel of the light detector. In some cases, bundling occurs by combining the ends of fibers 312a and 314a in parallel so that the outputs of fibers 312a and 314a can be detected together.

Multiple fibers or fiber doublets may be organized in logical strips. For example, if fibers 312a-312d are respectively bundled with fibers 314a-314d to form four fiber doublets, the four fiber doublets may be treated as strip 318. Similarly, if fibers 312e-312h are respectively bundled with fibers 314e-314h to form four fiber doublets, the four fiber doublets may be treated as strip 320. A strip may include more fibers or fiber doublets, such as 64 fibers or fiber doublets.

To further reduce the number of channels required in a light detector, similarly positioned fibers or fiber doublets in strips on a side of substrate 306 may be bundled together and connected to a single channel of the light detector. In this case, the location of the fiber or fiber doublet that generated photons within the strips in combination with the expected location of the pencil beam can be used to located the position of the pencil beam accurately to within, for example, 0.3 mm when using 1 mm$^2$ fibers. For example, the expected location of the pencil beam can be used to determine the expected strip where the proton will be and the fiber or fiber doublet that produces photons can be used to identify the location within the strip of the proton.

The two types of bundling described above (i.e., bundling adjacent fibers of different layers and bundling fibers or fiber doublets of different strips) can be used together or separately in different variations of the present technology.

Cross-section 302 depicts strips 318, 320, 322, and 324, which of which includes a plurality of fiber doublets. For example, strip 318 includes four fiber doublets made of fibers 312a-312d and fibers 314a-314d (e.g., fiber doublet 316), as described above. Similarly, strip 318 include fiber doublet 326, strip 320 include fiber doublet 328, strip 322 includes fiber doublet 330, and strip 324 includes fiver doublet 332. Because fiber doublets 318, 320, 322, and 324 are located at the same positions within strips 318, 320, 322, and 324, the outputs of these fiber doublets may be bundled together and connected to light detector 334 via a single channel (i.e., channel 336). Light detector 334 includes several channels (not shown) that are each connected to a group of fiber doublets that have the same position in the strips of the tracking detector. Light detector 334 provides electrical signals to computing system 338 representative of photons generated in the fibers of the tracking detector as received by the channels (e.g., channel 336) of light detector 334.

While an exemplary architecture of a tracking detector has been described in FIG. 3, the same bundling architecture could be used in other configurations of tracking detectors. For example, with respect to the tracking detector of FIG. 3, if fibers are rigid enough, fiber layers 308, 310, 312, and 314 could be bonded together to avoid using a substrate. As another example, fiber layers 308 and 310 could be placed on the same side of substrate 306 as fiber layers 312 and 314. In another example, fiber layers 308 and 310 could be placed on a separate substrate than fiber layers 312 and 314 and the two substrates could be placed next to each other.

Computing system 214 (FIG. 2) may implement embodiments of the present technology to produce images from data collected from the proton radiography system. In an example embodiment, computing system 214 implements a pipelined processing technique to produce images quickly from particle measurements.

Figure 4:
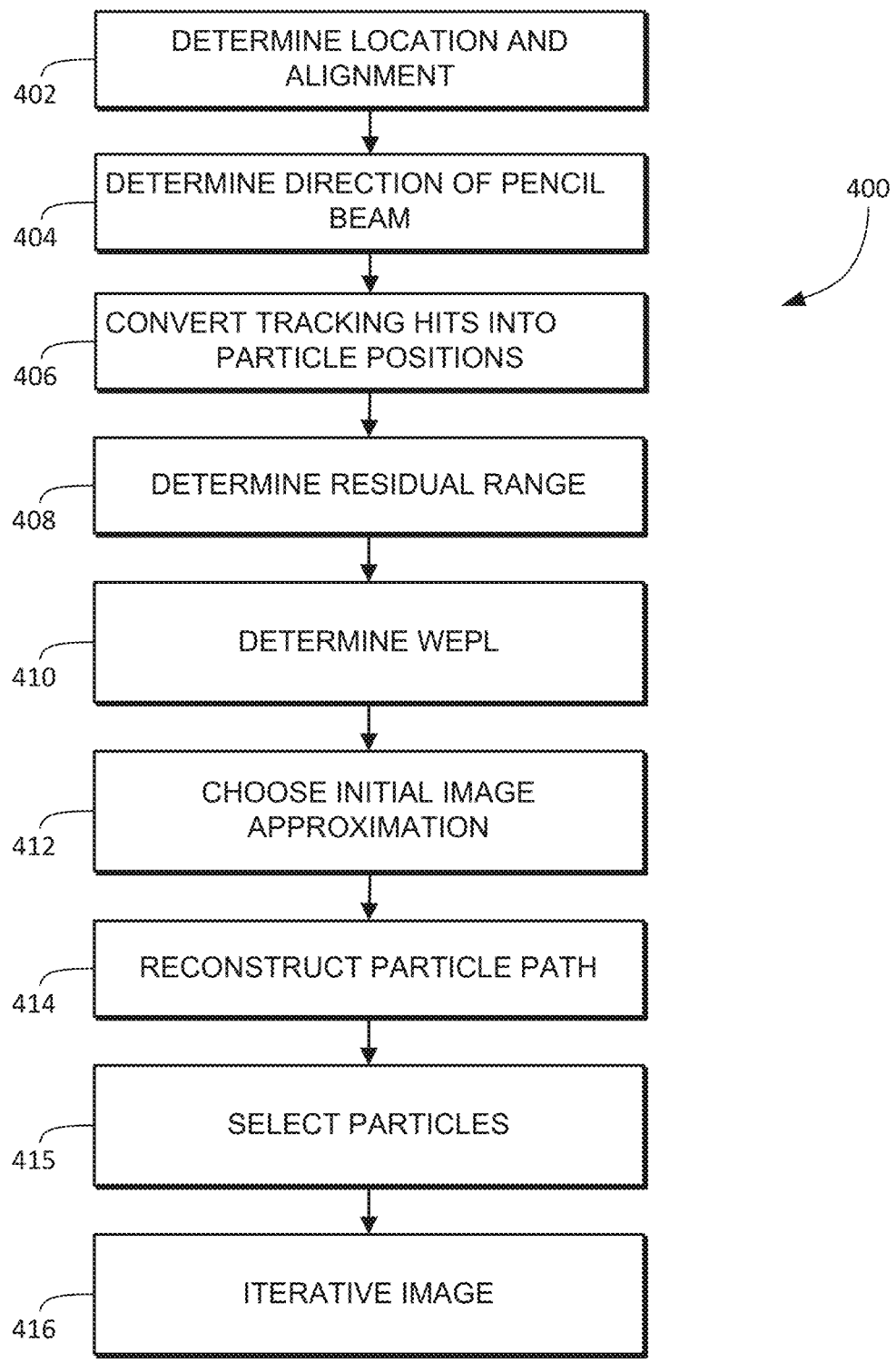
FIG. 4 is a flowchart of an exemplary process for generating a medical image.

FIG. 4 depicts flowchart of process 400 for an exemplary technique for producing a radiography or tomography image using a radiography system, such as proton radiography system 100. Process 400 describes an iterative technique that uses projective voxels, such as those depicted in FIG. 5, that represent the rays of the incoming proton directions. In other variations of the process, cubic voxels or other coordinate systems are used. Below, process 400 is described with respect to computing system 214 of proton radiography system 100. The process, however, is not limited to protons or radiography.

Figure 5:
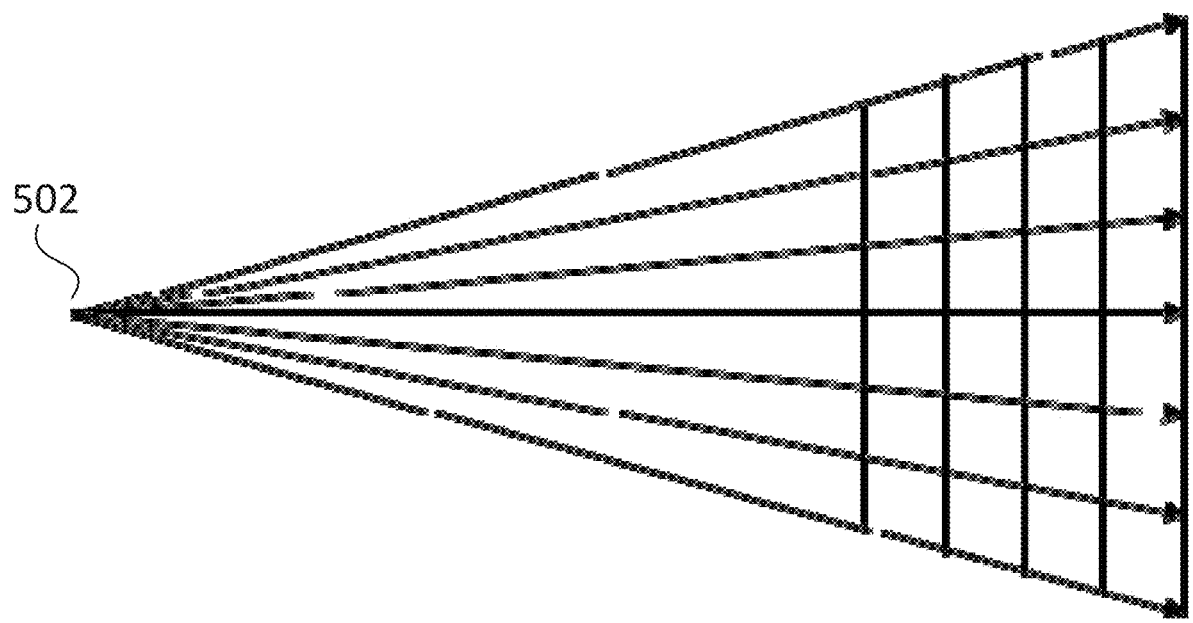
FIG. 5 shows a beam focal point and plurality of voxels.
Figure 6:
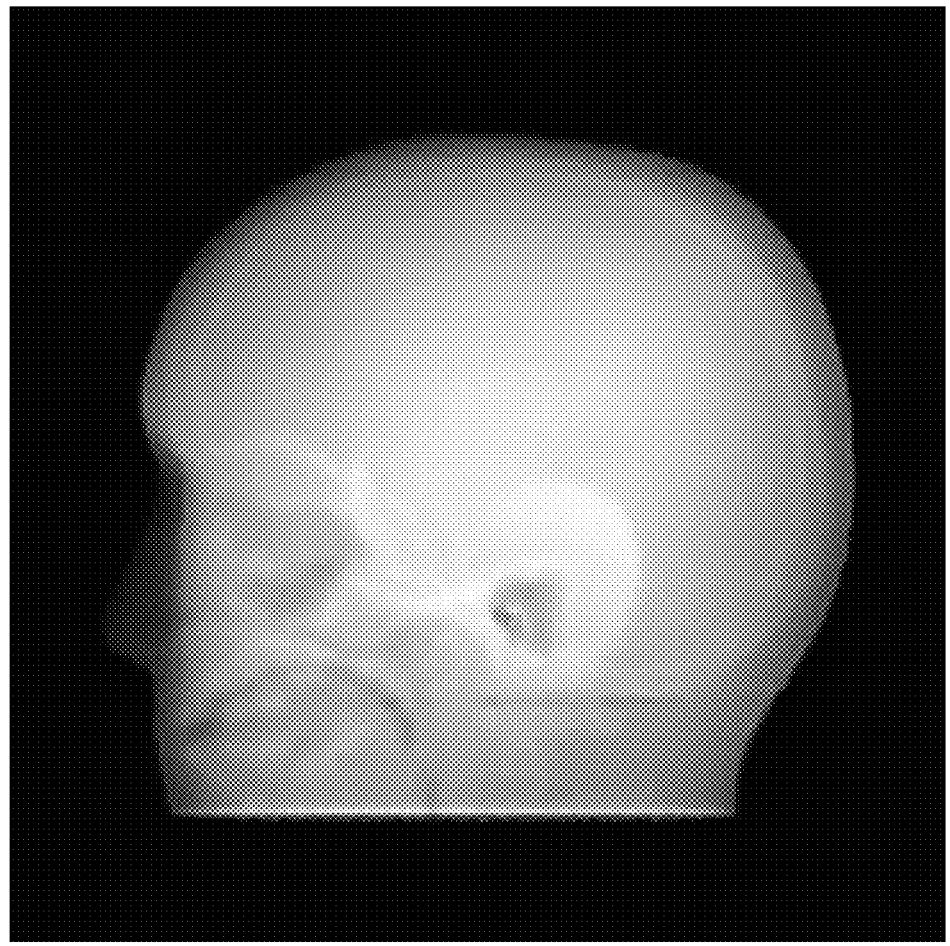
FIG. 6 shows an example medical image generated with embodiments of the present technology.

In block 402, computing system 214 determines a location and alignment of tracking detectors 106 and 108 (FIG. 1) in the beam system (e.g., a pencil beam). In FIG. 5, for example, a scanning pencil beam steers protons from focal point 502. The focal point can be scanned in the x- and y-directions. Ion treatment facilities have known focal points, and have calibrated steering to deliver beams to known coordinates in a plane at isocenter transverse to the beam system. Local coordinates in the tracking detector can be converted to coordinates relative to isocenter if the position of the tracking detector in the beam system is known.

A test pattern, consisting of a set of discrete proton spots, for example, may be used to align the tracking detectors 106 and 108 (or other configurations of tracking detectors) in system 100 (FIG. 1). An n×n array (e.g., n typically ranges from 2 to 5 but can take on other integers) of spots in the x-y plane, with about one thousand particles per spot (or on the order of thousands of particles per spot), can be used for this alignment. For radiography, this can be done from one direction. For tomography, two or more of these test patterns may be used, for example at 90 degrees difference. One option is to select the data for the test pattern as a sub-set of the imaging data. Or, the test pattern data may be dedicated data.

There may be up to 12 different rotation and translations of the upstream and downstream tracking planes (tracking planes 106 and 108, respectively). Specifically, three translations for each plane (i.e., along the x, y, and z axes) and three rotations for each plane (i.e., around each of the same axes). If the planes are relatively well aligned (e.g., so that the two planes move as a single body), this may be reduced to 6 alignment parameters. For a perfectly aligned detector, extrapolations of each spot will correctly converge to the known focal points in the x- and y-coordinates. Mismatches in any of the 12 parameters will have different effects in the extrapolation and patterns of hit detector elements. For example, if either tracking plane is rotated about the beam axis, scanning in the x- or y-directions will not result in constant x or y offsets in the tracking detector. For another example, if either tracking detector is not at the expected z-position along the beam, the focal points will appear displaced in the z-direction. For another example, if the detector is rotated about the x- or y-axes, or translated in x or y plane, the focal points will appear displaced in x- or y-directions. For another example, relative misalignments of the tracking detectors can cause the spots to appear not to converge to common focal points. These effects can be used to locate the detector in the beam system using the test pattern.

One alignment algorithm is an outgrowth of a theorem from projective geometry that any four-point in the projective plane (any four points, including points at infinity, no three of which are collinear) can be transformed to any other four-point using a projective transformation. Projective transformations preserve all straight lines and include scales, rotations and translations. 2D projective transformations include projections of 3D rotations onto 2D. In the 2D projective plane, points are represented by homogeneous 3-tuples [x y w] which are unique to a scale factor. To create a projective point from a Cartesian point, it is sufficient to set w=1. Conversion from projective points to Cartesian points is achieved (for points not at infinity) by dividing by w.

With the position of four measured points in the plane and four desired positions, it is possible to solve directly for a 3×3 matrix representing a projective transformation between the two sets. In essence, the transformation will take all points in the measured coordinate system and transform them to the desired coordinate system, in a way that is consistent with a combination of Euclidian transformations. This approach can be sensitive to position noise. In practice, sets of many corresponding point pairs are used to robustly derive a single projective transformation through non linear optimization, a process known as bundle adjustment in the computer vision community.

In one implementation, twenty-five well-separated spots of several thousand protons each are fired for the sake of alignment. The average spot position is calculated for each spot on both the upstream and downstream detector planes. These points are the measured points. Using the accelerator plan for the alignment along with knowledge of detector and beam geometry, positions are calculated for each theoretical spot center on the upstream and downstream detector planes. These are referred to as the ideal point positions. Projective transformations are calculated from the measured coordinate system to the ideal coordinate system for each of the detector planes.

The projective transformations are used in the image reconstruction step to take the intersections of each proton trace with the detector planes at unknown positions and orientations and convert the intersections into the corresponding coordinates with the detector planes at their ideal positions. Each coordinate transformation involves fourteen floating point operations per proton for each detector plane. This alignment-correction step is one of the pre-processing steps.

With this procedure, images can be directly reconstructed in the isocenter coordinate system of the beam scanning system, without relying on external alignment and other quality assurance steps. This enables a radiograph to be used for a patient alignment check, as well as for a check of integrated proton range.

A variation of this procedure can be used to check the tracking detector coordinate system. For example, if the tracking detector channels (e.g., channels connected to light detectors 212 and 222) consist of scintillating fibers or other types of strips, the tracking detector coordinates may be based on a survey of the strips as laid down in the construction process. Stepping the scanning pencil beam in the x- and y-directions while checking the average changes in the reconstructed detector coordinates can provide precise corrections to the survey.

In block 404, computing system 214 next determines a direction of the pencil beam spot for an individual particle. The measurement of the ion position in a tracking detector may produce several discrete solutions in order to save readout channels. Each solution corresponds to a different position and direction. If the direction of the pencil beam spot containing the ion is known, the correct solution may be chosen, and the position and direction of the ion will be known. There are several methods to resolving this ambiguity. It is possible to use more than one of these methods as a consistency check to reject events with problems such as nuclear scatters.

In one example, the time of the event is correlated with the expected steering of the ion beam at that time in the accelerator plan. The appearance of the first events can establish the starting time for both systems. The relative clock rates of the two systems can be calibrated with special runs using bursts of events spaced at regular times. The pattern of hit tracking channels vs. time can be monitored to update relative clock rates of the accelerator and detector system. For example, the beam can be turned off for short time gaps to enable checks of the relative timing.

In another example, different solutions will have different relative channels hits in the upstream and downstream tracking detectors. The solution can be established ion by ion, or found by averaging over many ions nearby in time.

As another example, the range detector may have position sensitivity, and can be used ion by ion, or by averaging over many ion nearby in time, to find the correct solution. This method may depend on the number and layout of photon detectors in the residual range detector.

In block 406, computing system 214 converts tracking detector hits into particle positions in the beam system while resolving ambiguities. Local tracking detector coordinates can be converted to coordinates in the beam system once the tracking detector alignment is known, as described above, and ambiguities are resolved, as described above. For the upstream tracker (e.g., tracking detector 106), the ion direction will also be known from the position. For the downstream tracker (e.g., tracking detector 108), multiple scattering may randomize the direction. A second downstream tracking detector (not shown) may provide the direction, otherwise only the position is known. Either setup can be used, with a second downstream tracking detector improving spatial resolution.

In block 408, computing system 214 converts hits in residual range detector 110 into calibrated residual range measurements. Given system dependent calibration procedures and position dependent corrections from the tracking system (which includes tracking detectors 106 and 108), using positions as described above, the residual range can be derived. Good events can be selected with a set of cuts to eliminate ions with nuclear interactions or other problems. Scattered events can sometimes leave additional hits in the tracking detectors. The residual range detector data can be checked for consistency with the ion position and consistency with nearby ions.

In block 410 the particle's initial kinetic energy is used to find the water equivalent path length (WEPL) for the particle. U.S. Patent Application Publication No. US2016/0338654 A1, which is hereby incorporated by reference, describes in detail one example of how the residual range of each particle is individually measured in the residual range detector after traversing the object being imaged. The initial total range of the proton before entering the system has a one-to-one relationship to the kinetic energy setting for the proton beam, which is set and calibrated by the proton therapy facility. The WEPL for the particle is the difference between the initial and residual ranges.

In block 412, optionally, computing system 214 chooses an initial approximation to the image before any particles are processed. This is not necessarily required (or can be taken as simply uniform material between the trackers), but can help convergence of the iterative algorithm and improve the accuracy of the particle path reconstruction. For either ion-based radiography or tomography, a diagnostic x-ray CT scan may be available, and can be used to define the boundary or "hull" of the patient. The standard conversion to stopping power can provide the initial approximation. In the case of ion radiography, a previous ion tomographic scan may be used instead. A visual hull could be used as well.

In some cases, a previous CT scan will be taken with the same patient couch as the current ion tomograph or radiograph. If not, it may be possible to remove the couch from the previous image and substitute the couch for the ion image. However, couches are designed to be low mass and even if the initial approximation to the couch is not perfect, the iterative algorithm should still converge.

The hull may be used for the initial approximation. If the hull is accurately known, it could also be used as a boundary to define which voxels participate in the iterative algorithm. Voxels outside the boundary could be defined with fixed values as air or as couch material, or the couch can be included inside the boundary. This would reduce computation time and improve convergence as much of the volume would not be sampled for density variations.

In the case of tomography, a preliminary image may be efficiently obtained from a filtered back projection, obtained with a straight-line approximation to the proton paths. This produces an image similar to the final image but with poorer spatial resolution, and may be used as the initial approximation. If a previous CT scan is available, it can be compared with this image to verify patient placement.

In the case of radiography, a preliminary image may be formed by extrapolating ions from the upstream detector to isocenter, binning them into pixels, and averaging their WEPL. If a previous CT scan is available, an expected preliminary image may be derived and compared to the actual preliminary image. This can be used to verify patient placement. If a previous CT scan is not available, an approximate hull can be constructed from the preliminary image combined with the WEPL, assuming water density to obtain the length along the beam path, and assumed to be centered on isocenter, or some other assumption based on inspection of the patient placement. Further refinement can be based on the amount of multiple scattering between the upstream and downstream planes. In the case of radiography, using protons from a single direction, the final step to obtain a 2D image requires a summing of voxels along columns in the direction of the proton rays, for example as illustrated in FIG. 5, thus collapsing an intermediate 3D map into the final 2D image.

An optional alternative to the approximate hull would be to use a separate hull for each proton, with length along the beam path matched to the WEPL of that proton. This length could assume water density, or if a geometric length is known from a previous image, fix the length but adjust the assumed density of the material. The shape could be a box large enough to contain any plausible proton path.

Procedures typically involve a careful placement and rotation of the patient in the beam system in order to correspond to a previous CT scan. A comparison of the preliminary proton images with the previous CT scan can verify patient placement and rotation. Transverse shifts will look like simple transverse offsets. When the proton beam is divergent, offsets along the beam direction will look like a difference in magnification. If the patient is rotated, the images might not correspond. It will be possible to prepare expected images assuming many different rotations to find the best match. Any significant shifts, offsets, or rotations should be taken into account in the initial approximation (or the patient should be repositioned).

In block 414, computing system 214 reconstructs the path of the particle between the tracking detectors 106 and 108. Given the hull and initial approximation, and the tracking measurements, standard techniques incorporating energy loss and multiple coulomb scattering can be used to find the Most Likely Path (MLP) of the proton within the hull. Previous uses of the MLP use step sizes of Vi voxel to detect voxels the proton has entered. A chord length can be assigned to each entered voxel. To save computational resources, a single effective mean chord length of the ion through each voxel may be used instead of computing a per voxel chord length for each ion. However, this procedure adds noise to the image, requiring more particles, more accelerator time, and more dose to the patient for a given image quality. As a result, when comparing images with the same image quality, the effective mean chord length approach may take more compute time.

In one example, an algorithm is used to avoid this extra source of image noise while still reducing compute time compared to other algorithms using per voxel chord lengths. Given the size of the transverse multiple scattering, a series of straight-line segments can be used, with each segment several voxels in length, with no significant loss of accuracy. The length of the segments can be constant through the imaging volume, or they can be scaled to the expected multiple scattering. This enables a much longer step size to be used for the MLP algorithm thus saving compute time. The interpolation between steps can be linear in (x,y,z) coordinates or linear in the (theta1, theta2, z) coordinates used in projective radiographs. With these straight line segments, it is straightforward to detect voxel boundaries and assign per voxel chord lengths. In the case of radiography, further simplification may be obtained by using step sizes corresponding to an integer number of voxels in z, so that each segment ends on a z-boundary of a voxel.

In another example of a method to calculate a variable chord length for each touched voxel:

The method does not involve calculation of intersections of line segments with sides of voxels. The method relies on the following stepping strategy through the reconstruction volume: each step is exactly one pixel along the beam direction; each step along the beam direction starts and end at the centers of two adjoining voxels. These conditions ensure that the step will always span at least two voxels. There is no need to check whether the step ends in the same or different voxel. If the step spans exactly two voxels, then the chord length assigned to each voxel is incremented by half the distance between the two end points. If the line joining the two end points spans more than two voxels, this is where the semi-exact calculation is done. The line segment is divided into a number of smaller sub-segments. In one implementation, we used twenty segments for each one mm step. Each sub-segment is then tested to which voxel it belongs; the chord length in that voxel is then incremented with the cumulative lengths of the sub-segments that were in that voxel. If a sub-segment spans across two voxels, the chord lengths of the two voxels are each incremented with half the length of the sub-segment. As the number of sub-segments increases, the chord length approximation improves, although at the expense of more computation time.

In some embodiments, the MLP algorithm relies on choosing endpoints for the particle path through the hull, which are the most likely intersections of the track with the hull. If the directions of the particles upstream and downstream of the hull are known, this involves a straightforward extrapolation of the path from the tracking detectors to the hull. In the case where there is only a single tracking detector downstream of the hull, providing a position measurement but not a direction measurement, some iteration may be needed to find the most likely intersection of the particle path with the hull. The MLP provides an expected direction for any assumed position of the particle. The downstream intersection of the path with the hull can be chosen as the point on the hull for which the MLP points to the downstream tracking measurement.

At block 415, computing system 214 uses iterative statistical cuts to eliminate events with outlier WEPL measurements due to nuclear interactions or other problems. First, events are sorted into two-dimensional bins according to MLP-estimated position on a given plane between the tracking detectors (typically intercepting isocenter). For tomography, the bins are three-dimensional, with rotation angle as the $3^{rd}$ dimension. The mean and standard deviation (sigma) of the WEPL are then calculated for each bin. Events with WEPL more than a certain number of sigma (typically two or three) from the mean are eliminated, and then a new mean and sigma are calculated from the remaining events. This process repeats until no more events are eliminated. The initial distribution of WEPL within a bin often shows a large number of "good" events clustered around the mean, followed by a long tail of "bad" events resulting from nuclear scattering at various depths in the range detector. This iterative cuts method has the effect of gradually cutting the tail until only the "good" events remain. This method can also be applied to measurements of lateral displacement between the upstream and downstream tracking planes. Cuts may be applied separately to events with different initial energies.

The range detector has lower and upper limits for residual ranges it can measure reliably, which are different from its physical boundaries. Not all ions that are detected in the range detector fall within this range. Because of range straggling, ions arrive in the range detector with a distribution of residual ranges, the mean of which is used to determine WEPL through the patient. In order to not skew the mean, it is important that the whole distribution be within the detector's measurable limits. A set of tighter limits can then be defined for the mean residual range. These limits are used to establish the minimum and maximum measurable WEPL for a given initial energy. When multiple energies are used, it is necessary to determine the areas of the patient for which each energy is valid, i.e. where the measured WEPL falls within the limits.

X-Ray CT data can be used to estimate WEPL through the patient and determine the regions where each energy should be used. However, there will be significant overlap due to the spread of the pencil beam and margins added for uncertainty. The overlap regions can be problematic where only a portion of the residual range distribution is measured. In areas where the WEPL is too high for the energy, some events on the higher end of the range distribution may still reach the range detector. In areas where the WEPL is too low for the energy, some events on the lower end of the distribution may be within the upper limit for residual range measurement. Including these events creates a biased WEPL distribution in the areas with overlapping energies, so it is necessary for the software to identify and remove these events.

At block 415, computing system 214 addresses this problem by first considering only events of the lowest energy, at which no events are expected to have a residual range too high to measure. Events of this energy that remain after statistical cuts are sorted into pixels based on position on the binning plane and rotation angle. For pixels containing a significant sample of these events—indicating the WEPL was not too high for at least some events to reach the range detector—the average WEPL is used to give a partial radiograph of the patient. Where this average WEPL is higher than the limit for the lowest energy, this energy is considered invalid. Higher energies are deemed invalid for any of these pixels in which the average WEPL is too low to be measured by the next-highest energy. Next, a partial radiograph is made using only events of the next-highest energy in the remaining pixels, and this is used to determine where the WEPL is too high for that energy and where it is too low for subsequent higher energies. The process continues until valid regions are defined for all energies. Events that are outside of their valid regions are excluded from the final reconstruction.

To save time, one option is to first use MLP only to determine position on the binning plane for the purpose of applying these cuts. The full MLP process including voxels and chord lengths can then be applied only to the remaining events.

At block 416, computing system 214 iteratively adjusts RSP values of voxels of the image to fit the data obtained from the blocks above (e.g., positional, directional, and energy data). Various algorithms can repeatedly going through the list of particles individually or in blocks and adjust the voxels to fit the particles. The system iteratively adjusts the image to fit the particles and find the final solution. The image can be for either radiography or tomography. In one example, the proton radiograph is formed by combining transverse position information from the tracking planes with range information from the residual range detector. Proton trajectories deviate from straight lines due to multiple Coulomb scattering, and forming the images with optimal spatial resolution is therefore more complicated than for x-ray radiographs. The iterative algebraic technique may use a matrix equation of the form $Ax=B$. The unknown RSP distribution is represented by x, which is a vector whose length M equals the total number of voxels in the reconstruction volume. A is an $N \times M$ matrix, with number of rows N equal to the number of proton trajectories and is often two or three orders of magnitude larger than M (i.e., the number of voxels, or unknowns). B is a vector of the measured ranges, or Water Equivalent Path Length (WEPL), of the N protons. Each row of A is of length M. However, a proton's trajectory is represented by assigning non-zero coefficients (chord-lengths) in A only to those voxels the proton traversed. For any given proton that is only a very small fraction of the total number of voxels in the reconstruction volume, typically only hundreds out of millions. The number of protons could range from a few millions to a few billions. Thus, the system of equations is very large, overdetermined, and sparse. The current solution involves repeated iteration over the list of protons, adjusting the RSP of the voxels traversed by a proton to agree with the measured residual range of the proton.

Figure 7:
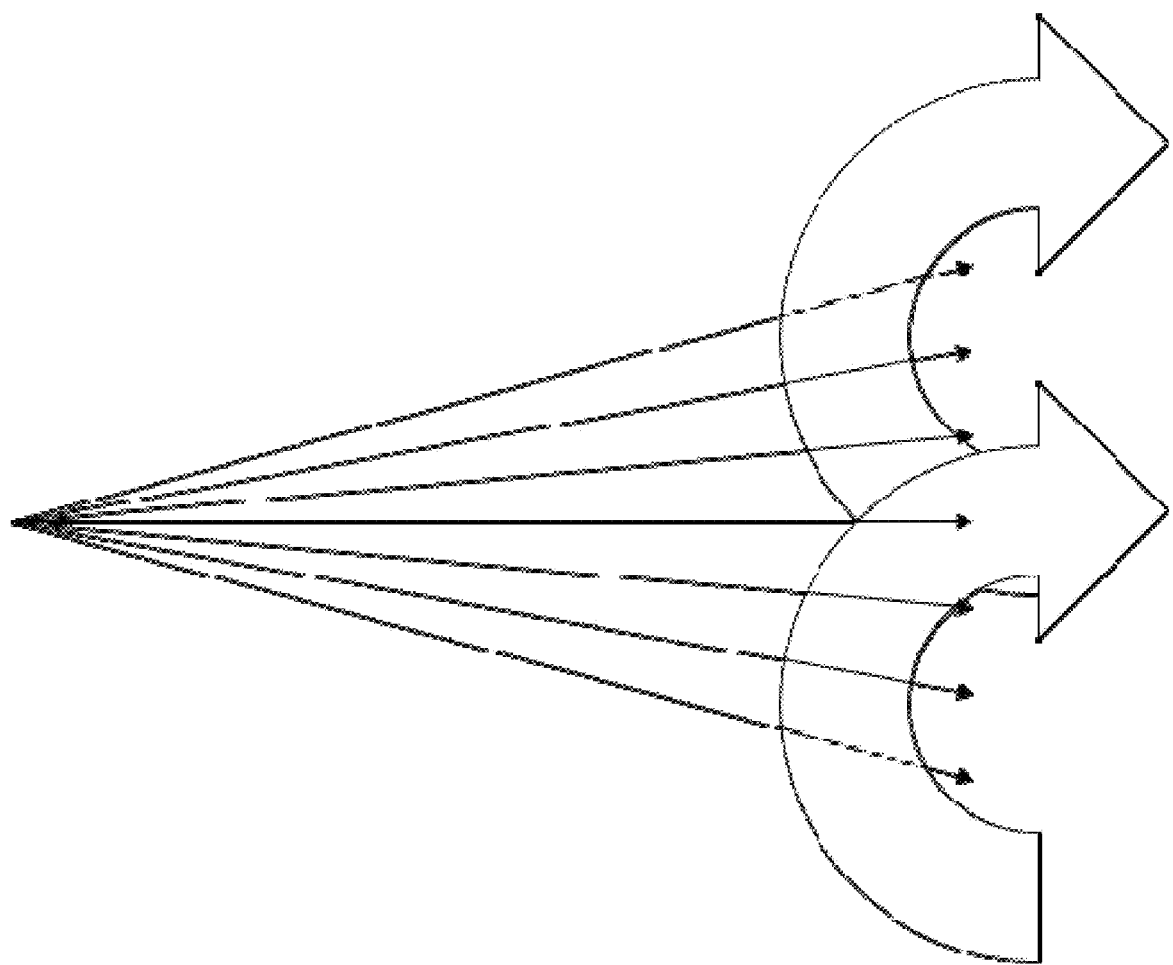
FIG. 7 shows using of two positions to scan entire patient in case of a large patient.

For radiography, it is not necessary to view the entire transverse size of the patient, though this may be desirable. For tomography, ions with all transverse positions and angles (180 degree range is sufficient) through the patient are required for a full 3D reconstruction. As shown in FIG. 7, this can be accomplished with two passes of the patient in the frame of the beam system, with a transverse shift of the patient between passes. For a fixed beam and a rotating patient, this is a simple transverse displacement of the rotating chair. In the case of a rotating gantry, the patient moves in small semi-circles in the frame of the treatment room. Before image reconstruction, the patient movement must be taken into account as a shift in the ion coordinates.

FIG. 7 depicts using of two positions to scan entire patient in case of a large patient (the same technique could be expanded to cover more than two positions). Each curved arrow represents the size of a patient turning around different axes. In the scanning beam frame with the patient rotating, one simply executes two rotations with the axis of rotation displaced transversely. In the frame with the scanning beam system on a gantry and turning with the gantry, the patient couch must be programmed to move in a small semi-circle as the gantry goes around the patient, however the picture would look the same as seen in the frame with the scanning beam system stationary.

The methods, systems, and devices discussed above are examples. Various configurations may omit, substitute, or add various method steps or procedures, or system components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory computer-readable medium such as a non-transitory storage medium. In some examples, one or more processors perform the described tasks.

Furthermore, the example embodiments described herein may be implemented as logical operations in a computing device in a networked computing system environment. The logical operations may be implemented as: (i) a sequence of computer implemented instructions, steps, or program modules running on a computing device; and (ii) interconnected logic or hardware modules running within a computing device.

EXAMPLES

Illustrative examples of the method and system disclosed herein are provided below. An embodiment of the method and system may include any one or more, and any combination of, the examples described below.

Example 1 is a computer-implemented method for generating a medical image. The method includes the step of determining a location and an alignment for a first tracking detector with respect to a particle beam system. A first position of a first particle generated from the beam system is determined, from a detected particle hit on the first tracking detector. The first direction of the first particle at the first tracking detector is determined. The method includes the step of determining a first residual range of the first particle from a detected particle hit on a residual range detector. A path for the first particle is reconstructed based on the location, the alignment, the first position, and the first direction. The medical image is generated based on the reconstructed path for the first particle and the first residual range of the first particle.

In Example 2, the subject matter of Example 1 is further configured such that generating the medical image includes iteratively adjusting a first value for a first voxel associated with the medical image and a second value for a second voxel associated with the medical image, wherein the adjusting is based on the first residual range.

In Example 3, the subject matter of Example 2 is further configured such that the first value and the second value are relative stopping power values.

In Example 4, the subject matter of Example 2 is further configured such that the first voxel is projected along the direction of the particle beam.

In Example 5, the subject matter of Example 1 is further configured to include selecting an initial image approximation for the medical image, wherein generating the medical image is further based on the initial image approximation.

In Example 6, the subject matter of Example 5 is further configured such that the initial image approximation is based on one or more of (i) data based on at least one of the first tracking detector, the beam system, or residual range detector, (ii) a CT image, or (iii) images from other modalities.

In Example 7, the subject matter of Example 2 is further configured to include determining a variable chord length for one or more touched voxels based on linear interpolations between voxel boundaries using steps larger than a voxel.

In Example 8, the subject matter of Example 1 is further configured such that determining the location and the alignment includes directing the beam at different positions around isocenter of the particle beam system.

In Example 9, the subject matter of Example 2 is further configured to include determining a variable chord length for one or more touched voxels based on subdividing steps that cross voxel boundaries into segments.

In Example 10, the subject matter of Example 1 is further configured to include correlating a time of the first particle hitting on the first tracking detector with an expected steering of the particle beam system at that time in the accelerator plan.

In Example 11, the subject matter of Example 1 is further configured to include iteratively eliminating particles based on a water equivalent path length (WEPL) measurement.

In Example 12, the subject matter of Example 1 is further configured to include selecting particles of an appropriate initial energy for a given region of the image.

Example 13 is one or more non-transitory computer-readable storage medium comprising a plurality of instructions that in response to being executed cause a computing device to: determine a location and an alignment for a first tracking detector with respect to a particle beam system; determine a first position of a first particle generated from the beam system, from a detected particle hit on the first tracking detector; determine a first direction of the first particle at the first tracking detector; determine a first residual range of the first particle from a detected particle hit on a residual range detector; reconstruct a path for the first particle based on the location, the alignment, the first position, and the first direction; and generate the medical image based on the reconstructed path for the first particle and the first residual range of the first particle.

In Example 14, the subject matter of Example 13 is further configured such that to generate the medical image includes to iteratively adjust a first value for a first voxel associated with the medical image and a second value for a second voxel associated with the medical image, wherein to adjust is based on the first residual range.

In Example 15, the subject matter of Example 14 is further configured such that the first value and the second value are relative stopping power values.

In Example 16, the subject matter of Example 14 is further configured such that the first voxel is projected along the direction of the particle beam.

In Example 17, the subject matter of Example 13 is further configured to include instructions to select an initial image approximation for the medical image, wherein to generate the medical image is further based on the initial image approximation.

In Example 18, the subject matter of Example 17 is further configured such that the initial image approximation is based on one or more of (i) data based on at least one of the first tracking detector, the beam system, or residual range detector, (ii) a CT image, or (iii) images from other modalities.

In Example 19, the subject matter of Example 14 is further configured to include instructions to determine a variable chord length for one or more touched voxels based on linear interpolations between voxel boundaries using steps larger than a voxel.

In Example 20, the subject matter of Example 13 is further configured such that to determine the location and the alignment includes to direct the beam at different positions around isocenter of the particle beam system.

In Example 21, the subject matter of Example 14 is further configured to include determining a variable chord length for one or more touched voxels based on subdividing steps that cross voxel boundaries into segments.

In Example 22, the subject matter of Example 13 is further configured to include correlating a time of the first particle hitting on the first tracking detector with an expected steering of the particle beam system at that time in the accelerator plan.

In Example 23, the subject matter of Example 13 is further configured to include iteratively eliminating particles based on a water equivalent path length (WEPL) measurement.

In Example 24, the subject matter of Example 13 is further configured to include instructions to select particles of an appropriate initial energy for a given region of the image.

Example 25 is a computing system for generating a medical image. The computing system includes one or more processors and a memory having a plurality of instructions stored thereon that, when executed by the one or more processors, causes the computing system to: determine a location and an alignment for a first tracking detector with respect to a particle beam system; determine a first position of a first particle generated from the beam system, from a detected particle hit on the first tracking detector; determine a first direction of the first particle at the first tracking detector; determine a first residual range of the first particle from a detected particle hit on a residual range detector; reconstruct a path for the first particle based on the location, the alignment, the first position, and the first direction; and generate the medical image based on the reconstructed path for the first particle and the first residual range of the first particle.

In Example 26, the subject matter of Example 25 is further configured such that to generate the medical image includes to iteratively adjust a first value for a first voxel associated with the medical image and a second value for a second voxel associated with the medical image, wherein to adjust is based on the first residual range.

In Example 27, the subject matter of Example 26 is further configured such that the first value and the second value are relative stopping power values.

In Example 28, the subject matter of Example 26 is further configured such that the first voxel is projected along the direction of the particle beam.

In Example 29, the subject matter of Example 25 is further configured to include instructions to select an initial image approximation for the medical image, wherein to generate the medical image is further based on the initial image approximation.

In Example 30, the subject matter of Example 29 is further configured such that the initial image approximation is based on one or more of (i) data based on at least one of the first tracking detector, the beam system, or residual range detector, (ii) a CT image, or (iii) images from other modalities.

In Example 31, the subject matter of Example 26 is further configured to include instructions to determine a variable chord length for one or more touched voxels based on linear interpolations between voxel boundaries using steps larger than a voxel.

In Example 32, the subject matter of Example 25 is further configured such that to determine the location and the alignment includes to direct the beam at different positions around isocenter of the particle beam system.

In Example 33, the subject matter of Example 26 is further configured to include instructions to determine a variable chord length for one or more touched voxels based on subdividing steps that cross voxel boundaries into segments.

In Example 34, the subject matter of Example 25 is further configured to include instructions to correlate a time of the first particle hitting on the first tracking detector with an expected steering of the particle beam system at that time in the accelerator plan.

In Example 35, the subject matter of Example 25 is further configured to include instructions to iteratively eliminate particles based on a water equivalent path length (WEPL) measurement.

In Example 36, the subject matter of Example 25 is further configured to include instructions to select particles of an appropriate initial energy for a given region of the image.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method for generating a medical image, the method comprising:
    determining a location and an alignment for a first tracking detector with respect to a particle beam system, wherein determining the location and the alignment includes converting local coordinates at which a calibrated steering beam is delivered to the first tracking detector to coordinates relative to isocenter of the particle beam system;
    determining a first position and a first initial kinetic energy of a first particle generated from the beam system, from a detected particle hit on the first tracking detector;
    determining a first direction of the first particle at the first tracking detector;
    determining a first residual range of the first particle from a detected particle hit on a residual range detector;
    reconstructing a path for the first particle directly in coordinates relative to isocenter of the particle beam system based on the location, the alignment, the first position, the first direction, and the first initial kinetic energy; and
    generating the medical image based on the reconstructed path for the first particle and the first residual range and the first initial kinetic energy of the first particle.

2. The method of claim 1, wherein generating the medical image includes iteratively adjusting a first value for a first voxel associated with the medical image and a second value for a second voxel associated with the medical image, wherein the adjusting is based on the first residual range.

3. The method of claim 2, wherein the first value and the second value are relative stopping power values.

4. The method of claim 2, wherein the first voxel is projected along the direction of the particle beam.

5. The method of claim 1, the method further comprising selecting an initial image approximation for the medical image, wherein generating the medical image is further based on the initial image approximation.

6. The method of claim 5, wherein the initial image approximation is based on one or more of (i) data based on at least one of the first tracking detector, the beam system, or residual range detector, (ii) a CT image, or (iii) images from other modalities.

7. The method of claim 2, further comprising determining a variable chord length for one or more touched voxels based on linear interpolations between voxel boundaries using steps larger than a voxel.

8. The method of claim 1, wherein determining the location and the alignment includes directing the beam at different positions around isocenter of the particle beam system.

9. The method of claim 2, further comprising determining a variable chord length for one or more touched voxels based on subdividing steps that cross voxel boundaries into segments.

10. The method of claim 1, further comprising correlating a time of the first particle hitting on the first tracking detector with an expected steering of the particle beam system at that time in the accelerator plan.

11. The method of claim 1, further comprising iteratively eliminating particles based on a water equivalent path length (WEPL) measurement and/or a measurement of lateral deflection between tracking planes.

12. The method of claim 1, further comprising selecting particles of an appropriate initial energy for a given region of the image.

13. The method of claim 1, wherein the path includes straight line interpolations between tracking detector hits and estimated particle entry and particle exit points on a geometric hull of an object to be imaged.

14. The method of claim 13, wherein the particle exit point from the geometric hull, for a case in which no exit direction is measured, is estimated as a point at which an exit direction points to the measured location on the posterior tracking plane.

15. The method of claim 1, wherein the reconstruction may include multiple sets of data taken with the patient in different transverse positions, combined into a single voxel reference frame by applying offsets to the measured positions in a detector reference frame.

16. One or more non-transitory computer-readable storage medium comprising a plurality of instructions that in response to being executed cause a computing device to:
    determine a location and an alignment for a first tracking detector with respect to a particle beam system, wherein determining the location and the alignment includes converting local coordinates at which a calibrated steering beam is delivered to the first tracking detector to coordinates relative to isocenter of the particle beam system;

determine a first position and a first initial kinetic energy of a first particle generated from the beam system, from a detected particle hit on the first tracking detector;

determine a first direction of the first particle at the first tracking detector;

determine a first residual range of the first particle from a detected particle hit on a residual range detector;

reconstruct a path for the first particle directly in coordinates relative to isocenter of the particle beam system based on the location, the alignment, the first position, the first direction, and the first initial kinetic energy; and generate the medical image based on the reconstructed path for the first particle and the first residual range and the first initial kinetic energy of the first particle.

17. The one or more non-transitory computer-readable storage medium of claim 16, wherein to generate the medical image includes to iteratively adjust a first value for a first voxel associated with the medical image and a second value for a second voxel associated with the medical image, wherein to adjust is based on the first residual range.

18. The one or more non-transitory computer-readable storage medium of claim 17, wherein the first value and the second value are relative stopping power values.

19. The one or more non-transitory computer-readable storage medium of claim 17, wherein the first voxel is projected along the direction of the particle beam.

20. The one or more non-transitory computer-readable storage medium of claim 16, further comprising instructions to select an initial image approximation for the medical image, wherein to generate the medical image is further based on the initial image approximation.

21. The one or more non-transitory computer-readable storage medium of claim 20, wherein the initial image approximation is based on one or more of (i) data based on at least one of the first tracking detector, the beam system, or residual range detector, (ii) a CT image, or (iii) images from other modalities.

22. The one or more non-transitory computer-readable storage medium of claim 17, further comprising instructions to determine a variable chord length for one or more touched voxels based on linear interpolations between voxel boundaries using steps larger than a voxel.

23. The one or more non-transitory computer-readable storage medium of claim 16, wherein to determine the location and the alignment includes to direct the beam at different positions around isocenter of the particle beam system.

24. The one or more non-transitory computer-readable storage medium of claim 17, further comprising determining a variable chord length for one or more touched voxels based on subdividing steps that cross voxel boundaries into segments.

25. The one or more non-transitory computer-readable storage medium of claim 16, further comprising correlating a time of the first particle hitting on the first tracking detector with an expected steering of the particle beam system at that time in the accelerator plan.

26. The one or more non-transitory computer-readable storage medium of claim 16, further comprising iteratively eliminating particles based on a water equivalent path length (WEPL) measurement and/or a measurement of lateral deflection between tracking planes.

27. The one or more non-transitory computer-readable storage medium of claim 16, further comprising instructions to select particles of an appropriate initial energy for a given region of the image.

28. The one or more non-transitory computer-readable storage medium of claim 16, wherein the path includes straight line interpolations between tracking detector hits and estimated particle entry and particle exit points on a geometric hull of an object to be imaged.

29. The one or more non-transitory computer-readable storage medium of claim 28, wherein the particle exit point from the geometric hull, for a case in which no exit direction is measured, is estimated as a point at which an exit direction points to the measured location on the posterior tracking plane.

30. The one or more non-transitory computer-readable storage medium of claim 16, wherein the reconstruction may include multiple sets of data taken with the patient in different transverse positions, combined into a single voxel reference frame by applying offsets to the measured positions in a detector reference frame.

31. A computing system for generating a medical image, the computing system comprising:

one or more processors;

a memory having a plurality of instructions stored thereon that, when executed by the one or more processors, causes the computing system to:

determine a location and an alignment for a first tracking detector with respect to a particle beam system, wherein determining the location and the alignment includes converting local coordinates at which a calibrated steering beam is delivered to the first tracking detector to coordinates relative to isocenter of the particle beam system;

determine a first position and a first initial kinetic energy of a first particle generated from the beam system, from a detected particle hit on the first tracking detector;

determine a first direction of the first particle at the first tracking detector;

determine a first residual range of the first particle from a detected particle hit on a residual range detector;

reconstruct a path for the first particle directly in coordinates relative to isocenter of the particle beam system based on the location, the alignment, the first position, the first direction, and the first initial kinetic energy; and generate the medical image based on the reconstructed path for the first particle and the first residual range and the first initial kinetic energy of the first particle.

32. The computing system of claim 31, wherein to generate the medical image includes to iteratively adjust a first value for a first voxel associated with the medical image and a second value for a second voxel associated with the medical image, wherein to adjust is based on the first residual range.

33. The computing system of claim 32, wherein the first value and the second value are relative stopping power values.

34. The computing system of claim 32, wherein the first voxel is projected along the direction of the particle beam.

35. The computing system claim 31, further comprising instructions to select an initial image approximation for the medical image, wherein to generate the medical image is further based on the initial image approximation.

36. The computing system of claim 35, wherein the initial image approximation is based on one or more of (i) data based on at least one of the first tracking detector, the beam system, or residual range detector, (ii) a CT image, or (iii) images from other modalities.

37. The computing system of claim 32, further comprising instructions to determine a variable chord length for one or more touched voxels based on linear interpolations between voxel boundaries using steps larger than a voxel.

38. The computing system of claim 31, wherein to determine the location and the alignment includes to direct the beam at different positions around isocenter of the particle beam system.

39. The computing system of claim 32, further comprising instructions to determine a variable chord length for one or more touched voxels based on subdividing steps that cross voxel boundaries into segments.

40. The computing system of claim 31, further comprising instructions to correlate a time of the first particle hitting on the first tracking detector with an expected steering of the particle beam system at that time in the accelerator plan.

41. The computing system of claim 31, further comprising instructions to iteratively eliminate particles based on a water equivalent path length (WEPL) measurement and/or a measurement of lateral deflection between tracking planes.

42. The computing system of claim 31, further comprising to instructions to select particles of an appropriate initial energy for a given region of the image.

43. The computing system of claim 31, wherein the path includes straight line interpolations between tracking detector hits and estimated particle entry and particle exit points on a geometric hull of an object to be imaged.

44. The computing system of claim 43, wherein the particle exit point from the geometric hull, for a case in which no exit direction is measured, is estimated as a point at which an exit direction points to the measured location on the posterior tracking plane.

45. The computing system of claim 31, wherein the reconstruction may include multiple sets of data taken with the patient in different transverse positions, combined into a single voxel reference frame by applying offsets to the measured positions in a detector reference frame.

46. The method of claim 1 wherein the medical image is a two-dimensional map formed by binning particles into pixels based on extrapolated positions at a plane, and averaging the WEPL measurements of the particles within each pixel.

* * * * *